United States Patent
Brailovski et al.

(10) Patent No.: US 10,342,554 B2
(45) Date of Patent: Jul. 9, 2019

(54) LIMB SPARING IN MAMMALS USING PATIENT-SPECIFIC ENDOPROSTHESES AND CUTTING GUIDES

(71) Applicants: SOCOVAR, L.P., Montreal (CA); Colorado State University Research Foundation, Fort Collins, CO (US); Universite de Montreal, Montreal (CA)

(72) Inventors: Vladimir Brailovski, Montreal (CA); Yvan Petit, St-Mathieu de Beloeil (CA); Bertrand Lussier, Bromont (CA); Bernard Seguin, Fort Collins, CO (US); Martin Brummund, Montreal (CA); Anatolie Timercan, LaSalle (CA)

(73) Assignees: SOCOVAR, L.P., Montreal (CA); Colorado State University Research Foundation, Fort Collins, CO (US); Universite de Montreal, Montreal (CA)

( * ) Notice: Subject to any disclaimer, the term of this patent is extended or adjusted under 35 U.S.C. 154(b) by 66 days.

(21) Appl. No.: 15/620,502

(22) Filed: Jun. 12, 2017

(65) Prior Publication Data

US 2017/0360453 A1 Dec. 21, 2017

Related U.S. Application Data

(60) Provisional application No. 62/351,533, filed on Jun. 17, 2016.

(51) Int. Cl.
*A61B 17/15* (2006.01)
*A61B 17/17* (2006.01)
(Continued)

(52) U.S. Cl.
CPC .......... *A61B 17/1739* (2013.01); *A61B 17/15* (2013.01); *A61B 17/151* (2013.01);
(Continued)

(58) Field of Classification Search
CPC ............ A61B 17/151; A61B 2034/108; A61B 17/1739; A61B 2034/105
See application file for complete search history.

(56) References Cited

U.S. PATENT DOCUMENTS

| 5,935,128 A | * | 8/1999 | Carter | ............. A61B 17/15 606/102 |
|---|---|---|---|---|
| D536,453 S | | 2/2007 | Young et al. | |

(Continued)

FOREIGN PATENT DOCUMENTS

| WO | 07092481 | 8/2007 |
|---|---|---|
| WO | 2009105535 | 8/2009 |
| WO | 2015131234 | 9/2015 |

OTHER PUBLICATIONS

Straw RC, Withrow SJ: Limb-sparing surgery versus amputation for dogs with bone tumors. Vet Clin North Am Small Anim Pract Jan. 1996; 26:135-143.

(Continued)

*Primary Examiner* — Christian A Sevilla

(57) ABSTRACT

A cutting guide for guiding a cut in a radius, the radius being adjacent to an ulna, the cutting guide comprising: a cut guiding portion, an opposed ulnar mounting portion and a linking portion extending therebetween; the cutting guide being delimited by a cutting guide peripheral surface defining a bone facing portion, the bone facing portion being contoured to match the shape of the radius and ulna.

4 Claims, 4 Drawing Sheets

(51) Int. Cl.
*A61B 34/10* (2016.01)
*A61B 17/80* (2006.01)
*A61F 2/28* (2006.01)
A61B 17/56 (2006.01)
A61F 2/30 (2006.01)

(52) U.S. Cl.
CPC ...... *A61B 17/1728* (2013.01); *A61B 17/8061* (2013.01); *A61B 34/10* (2016.02); *A61F 2/28* (2013.01); *A61B 2017/568* (2013.01); *A61B 2034/105* (2016.02); *A61B 2034/108* (2016.02); *A61F 2/30942* (2013.01); *A61F 2002/307* (2013.01); *A61F 2002/30578* (2013.01); *A61F 2002/30948* (2013.01); *A61F 2002/30952* (2013.01); *A61F 2002/30962* (2013.01)

(56) References Cited

U.S. PATENT DOCUMENTS

| | | |
|---|---|---|
| 7,282,053 B2 | 10/2007 | Orbay |
| 9,113,914 B2 | 8/2015 | Carroll et al. |
| 9,186,256 B2 | 11/2015 | Shultz et al. |
| 2002/0082604 A1 | 6/2002 | Abdelgany et al. |
| 2002/0198600 A1 | 12/2002 | Kuntz |
| 2009/0198244 A1* | 8/2009 | Leibel ............... A61B 17/15 606/99 |
| 2011/0238073 A1 | 9/2011 | Lang et al. |
| 2011/0269100 A1 | 11/2011 | Furrer et al. |
| 2011/0304332 A1 | 12/2011 | Mahfouz |
| 2012/0158001 A1 | 6/2012 | Burdulis, Jr. et al. |
| 2012/0277751 A1 | 11/2012 | Catanzarite et al. |
| 2013/0292870 A1 | 11/2013 | Roger |
| 2014/0257309 A1 | 9/2014 | Aram et al. |
| 2015/0342643 A1 | 12/2015 | Fitzpatrick |

OTHER PUBLICATIONS

Kuntz Ca, Assel in TL, Dernell WS, et al: Limb salvage surgery for osteosarcoma of the proximal humerus: outcome in 17 dogs. Vet Surg Sep. 1998 ;27:417-422, 1998.
Norton C, Drenen CM, EMMS SG: Subtotal scapulectomy as the treatment for scapular tumour in the dog: a report of six cases. Aust Vet J;Oct. 2006; 84:364-366.
Trout NJ, Pavletic MM, Kraus KH: Partial scapulectomy for management of sarcomas in three dogs and two ;cats. J Am Vet Med Assoc; Sep. 1995; 207:585-587.
Montinaro V, Boston SE, Buracco P, et al: Clinical outcome of 42 dogs with scapular tumors treated by scapulectomy: a Veterinary Society of Surgical Oncology (VSSO) retrospective study (1995-2010). Vet Surg Nov. 2013; 42:943-950.
Sivacolundhu RK, Runge JJ, Donovan Ta, et al: Ulnar osteosarcoma in dogs: 30 cases (1992-2008). J Am Vet Med Assoc Jul. 2013; 243:96-101.
Kirpensteijn J, Steinheimer D, Park Rd, et al: Comparison of cemented and non-cemented allografts in logs with osteosarcoma. Vet Comp Orthop Traumatol Nov. 1998; 11:178-184.

Lascelles BD, Dernell WS, Correa Mt, et al: Improved survival associated with postoperative wound Infection in dogs treated with limb-salvage surgery for osteosarcoma. Ann Surg Oncol Oct. 2005; 12:1073-1083.
Withrow SJ, Liptak Jm, Straw RC, et al: Biodegradable cisplatin polymer in limb-sparing surgery for canine osteosarcoma. Ann Surg Oncol ;Jul. 2004; 11:705-713.
Liptak JM DW, Ehrhart N, Withrow SJ, Seguin B, Walsh PJ, Kuntz Ca: Canine appendicular osteosarcoma: curative-intent treatment. Compendium on Continuing Education;Mar. 2004; 26:186-196.
Liptak JM, Dernell WS, Ehrhart N, et al: Cortical allograft and endoprosthesis for limb-sparing surgery in dogs with distal radial osteosarcoma: a prospective clinical comparison of two different limb-sparing techniques. Vet Surg Aug. 2006; 35:518-533.
Ehrhart N: Longitudinal bone transport for treatment of primary bone tumors in dogs: technique description and outcome in 9 dogs. Vet Surg Jan. 2005; 34:24-34.
Tommasini Degna M, Ehrhart N, Feretti A, et al: Bone Transport Osteogenesis for Limb Salvage Following Resection of Primary Bone Tumors: Experience with Six Cases (1991-1996). Vet Comp Orthop Traumatol Feb. 2000; 13:18-22.
Boston SE, Duerr F, Bacon N, et al: Intraoperative radiation for limb sparing of the distal aspect of the radius without transcarpal plating in five dogs. Vet Surg; Jun. 2007; 36:314-323.
Buracco P, Morello E, Martano M, et al: Pasteurized tumoral autograft as a novel procedure for limb sparing in the dog: A clinical report. Vet Surg;Nov. 2002; 31:525-532.
Hodge SC, Degner D, Walshaw R, et al: Vascularized ulnar bone grafts for limb-sparing surgery for the treatment of distal radial osteosarcoma. J Am Anim Hosp Assoc 47Mar. 2011; 98-111.
Seguin B, Walsh PJ, Mason Dr, et al: Use of an ipsilateral vascularized ulnar transposition autograft for limb-sparing surgery of the distal radius in dogs: an anatomic and clinical study; Jan. 2003; Vet Surg 32:69-79.
Seguin B, Walsh PJ: Novel limb sparing technique for the distal radial site in dogs: lateral manus translation, Proceedings, European College of Veterinary Surgeons Annual Scientific Meeting, Nantes, France, Jun. 2009.
Harrysson OA, Marcellin-Little D, Horn T: Applications of Metal Additive Manufacturing in Veterinary Orthopedic Surgery. Feb. 2015; JOM 67:647-654.
Liu X, Chu PK, Ding C: Surface modification of titanium, titanium alloys, and related materials for biomedical applications. Materials Science and Engineering: R: Reports; Dec. 2004; 47:49-121.
M. Perez MB, D. Espalin, R. Winker, T. Hoppe, F. Medina, and R. Wicker: Sterilization of FDM-Manufactured Parts, in 23rd Int. Solid Freeform Fabr. Symp., Aug. 2011; vol., 2012, pp. 285-296.
Pooya Ha, Séguin B, Mason Dr, et al: Biomechanical Comparison of Cortical Radial Graft versus Ulnar Transposition Graft Limb-Sparing Techniques for the Distal Radial Site in Dogs. Veterinary Surgery Jul. 2004;33:301-308.
Ehrhart NP, Ryan SD, Fan TM: Tumors of the skeletal system, in Withrow SJ VD, p. Rl (ed): Small Animal clinical Oncology, vol. St-Louis, Nov. 2012 Elsevier, pp. 463-503.
Wilke VL, Robinson DA, Evans RB, et al: Estimate of the annual economic impact of treatment of cranial cruciate ligament injury in dogs in the United States. J Am Vet Med Assoc Nov. 2005; 227:1604-1607.
Rowell JL, Mccarthy Do, Alvarez CE: Dog models of naturally occurring cancer. Trends Mol Med Mar. 2011; 17:380-388.

* cited by examiner

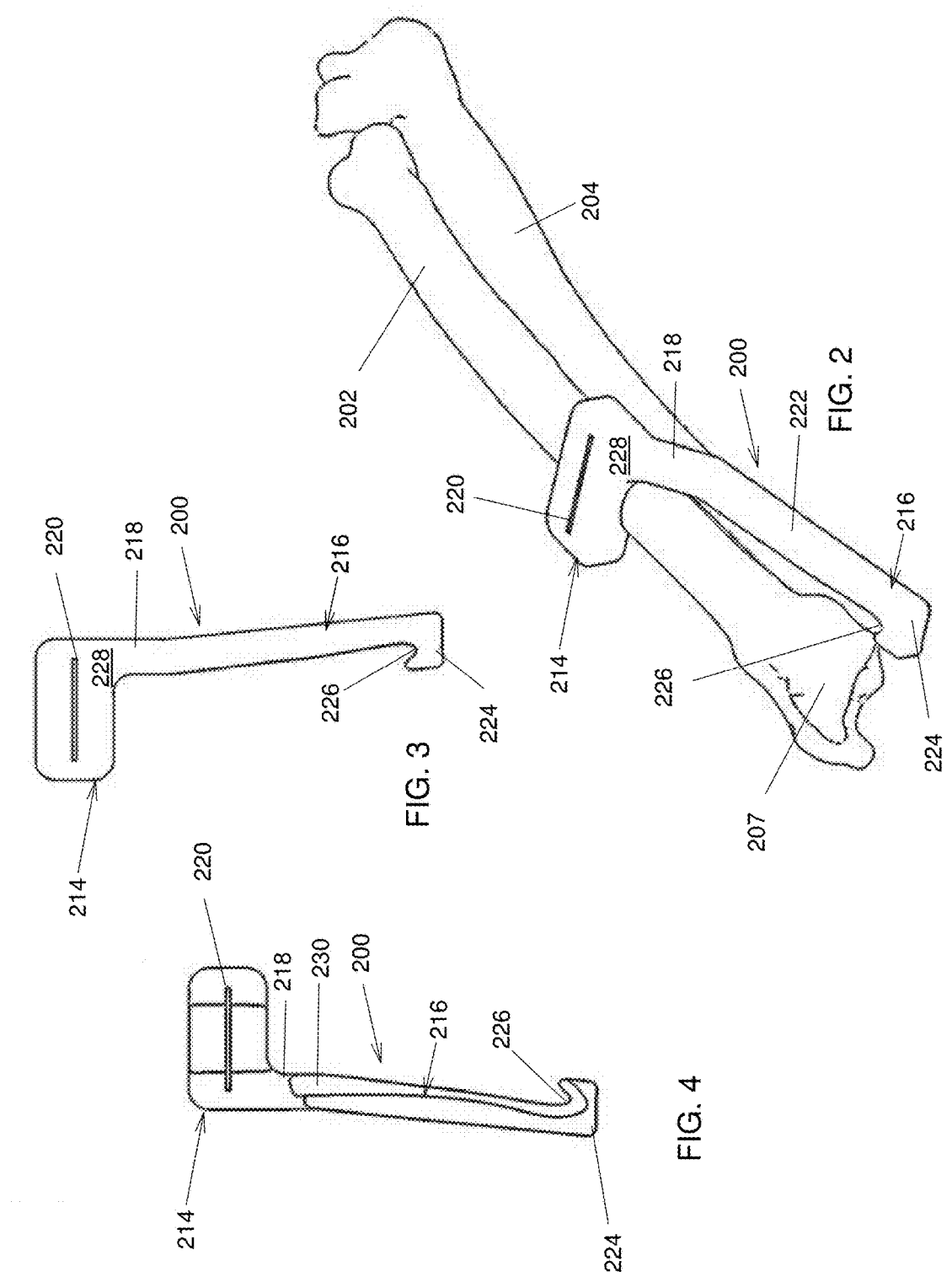

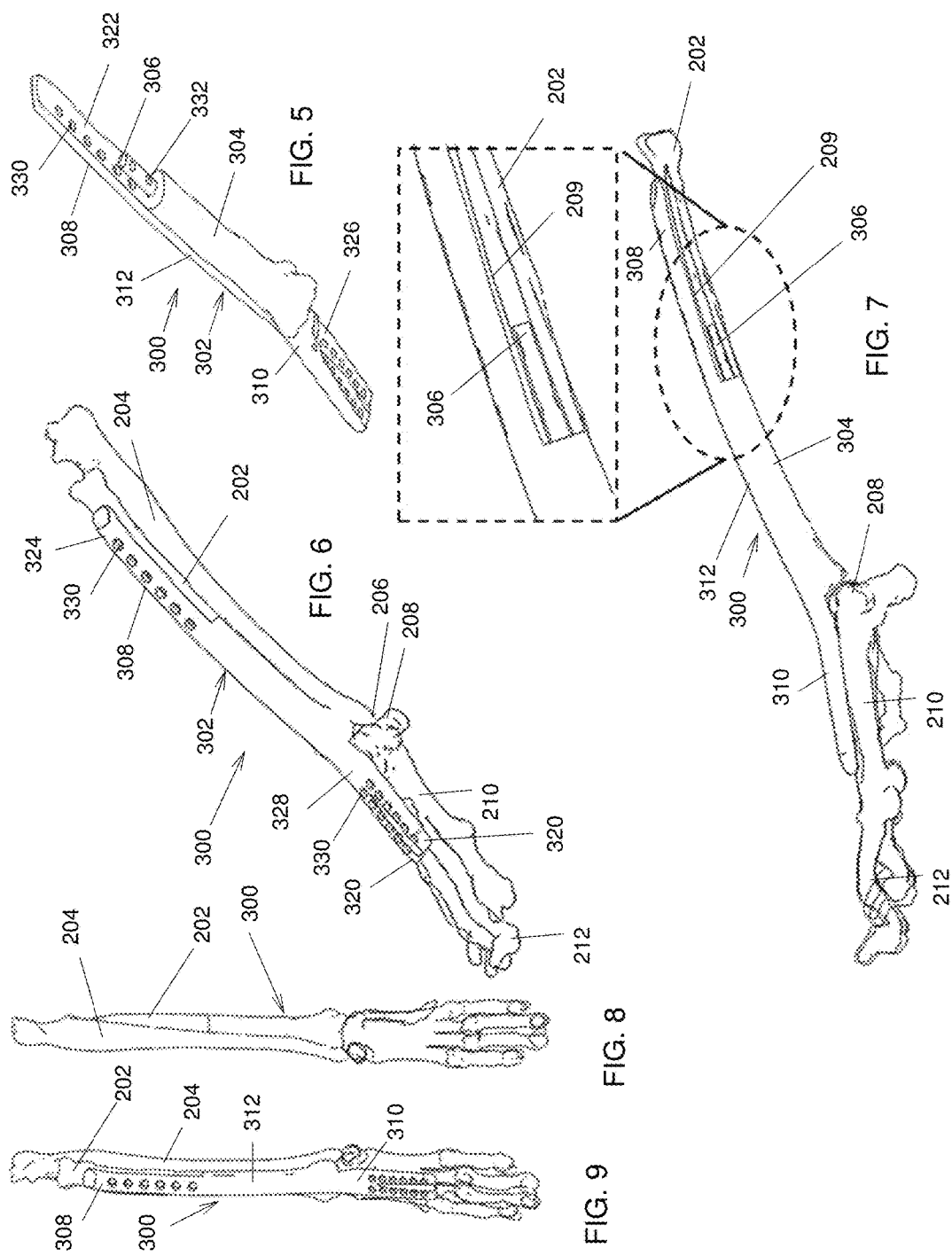

LIMB SPARING IN MAMMALS USING PATIENT-SPECIFIC ENDOPROSTHESES AND CUTTING GUIDES

FIELD OF THE INVENTION

The present invention relates to the art of medical treatments. More specifically, the present invention is concerned with limb sparing in mammals using patient-specific endoprostheses and cutting guides.

BACKGROUND

Osteosarcoma of the distal radius is the most common type of bone tumor in dogs and affects over 10 000 dogs each year. To date, several surgical limb sparing techniques exist which result in functionally good outcome. Nevertheless, post-surgery complication rates with these techniques remain significant. Complications most commonly encountered include implant or bone failure, infection and tumor recurrence.

Limb sparing has been performed for over 25 years in dogs afflicted by primary bone tumors of the appendicular skeleton.[1,2] Limb sparing consists in removing the segment of bone bearing the primary tumor and using internal or external fixation to the remaining bones with or without segmental bone replacement, resulting in a salvaged functional limb. Although amputation remains the standard of care to address the local tumor, some dogs are not good candidates for amputation because of concurrent orthopedic or neurologic disease or some owners are opposed to having an amputation performed. The prognosis for survival is the same with amputation of the limb or limb sparing.[1,2] The anatomic sites most amendable to limb sparing are the distal aspect of the radius, the ulna distal to the interosseous ligament, and the scapula. The distal aspect of the ulna and the scapula are technically simpler because they do not require reconstruction[3-6] and are not considered true limb sparing procedures by many for this reason.

The most common anatomic site where limb sparing is performed in dogs is the distal radius. Historically, the most commonly performed technique has been the use of an allograft[7-11] to replace the critical bone defect created by segmental osseous excision. Although limb function is good to excellent in 75%-90% of dogs with the allograft technique,[1,11] the complication rate is significant. The most common complications with this technique are infection, implant related problems, and local recurrence. Infection is reported in up to 70% of limbs,[7] implant problems in up to 60%,[7] and local recurrence in up to 60% as well.[9] The allograft technique requires either the maintenance of a bone bank, which is time consuming and costly, or purchasing an allograft from a commercial site (https://vtsonline.com, for example) on a case by case basis.[3]

Other surgical techniques have been developed for limb-sparing of the distal radial site. These techniques include: use of an endoprosthesis,[11] distraction osteogenesis by bone transport,[12,13] intraoperative extracorporeal radiotherapy,[14] tumoral autograft pasteurization,[15] microvascular ulnar autograft,[16] ulnar rollover transposition,[16,17] and lateral manus translation.[18] Disadvantages of the bone transport osteogenesis procedure are the need for repeated multiple daily distractions of the apparatus and the significant amount of time required to fill the defect after tumor removal (up to 5 months).[13] Microvascular autograft techniques require specialized equipment and training for the surgical team and add significant time to the procedure to allow microvascular anastomosis. Techniques that require the ipsilateral distal portion of the ulna to remain intact (ulnar rollover transposition and lateral manus translation) cannot be performed when the tumor invades the ulna.

The use of endoprosthesis carries the strong advantage of simplicity compared to the use of an allograft and consequently it is time-saving. The use of standard fixation plates bears limitations: they form a lap-type connection with the remaining bones, which is eccentric to the applied load, thus not offering an adequate support for the salvaged limb. Moreover, standard plates need contouring in the operation room to approach the natural curvature of the limb, thus extending the operation time.

Some of the above-mentioned problems are also present in other mammals, including other animals and humans.

Accordingly, there is a need in the industry to provide novel limb sparing techniques.

SUMMARY OF THE INVENTION

The use of personalized implants appears to be an ideal solution to reduce the above-mentioned drawbacks[19] of conventional limb sparing techniques. Notably, three problems related to limb sparing are: high infection rate, implant/bone failure and local recurrence of the tumor. The present invention uses computer aided reconstruction and design methods as well as two independent 3D printing techniques to design and manufacture personalized endoprostheses and cutting guides. The patient specific design approach promises to provide patients with highly resilient implants and decreased failure risk due to more physiological loading. Furthermore, the most natural implant fit will significantly reduce surgical time which reduces the risk of infection. Lastly, the rapidity of the proposed workflows enables shorter turnover times which will help in decreasing the risk of local recurrence.

Regarding implant/bone failure, the most important reason for this complication is that the currently available implants are not properly designed to withstand the forces generated through the limb with limb sparing and do not fit perfectly to the bony configuration. Currently, veterinary surgeons are trying to adapt the implants available to each patient but ultimately they never fit perfectly well and lead to exaggerated loads on both the implants and bones. By producing patient-specific implants, we have the opportunity to make these implants fit as perfectly as can be for each patient and to optimize their design to better withstand the loads transmitted through the limb. Instead of having the patient fit the implant, we would have the implant fit each patient.

Regarding high infection rate, the main reasons for infection are surgical trauma to the local environment, duration of the surgery, decreased local immunity from the presence of the tumor, use of adjuvant chemotherapy, or implantation of a large non-viable bone graft. The use of personalized implants allows the surgical time to be significantly decreased because there will be no need to modulate/bend the implant to fit a local geometry, thus reducing the risk of infection. Moreover personalized implants having a better fit could be thinner than conventional plates, thus contributing to reducing the risk of infection even further, as a link between insufficient soft tissue coverage at the implant site and infection has been reported.[10]

Regarding local recurrence, it has been shown that local delivery of a chemotherapeutic agent can reduce the risk of local recurrence[9]. 3D printing facilitates controlled surface texturing of endoprostheses and subsequent bioactiviation[20] which could aid in locally delivering chemotherapeutics.

Generally speaking, the proposed method for limb sparing uses the following steps. While the proposed method herein is used in the context of dogs, this method is also applicable in other animals, such as humans for example. Anatomically correct geometrical reconstruction of both forelimbs is the first step for the design of the custom-made endoprosthesis. Commonly, in dogs suffering from osteosarcoma, both the affected and normal contralateral limbs are imaged simultaneously. The affected limb serves to determine the length of the excised portion of the radius and to design the cutting guide. The unaffected limb is utilized to design the bone replica portion of the endoprosthesis. Subsequently, a mirrored image of the replica is generated to bridge the bone defect created during surgery. The mirrored geometry is then examined and, if necessary, adjusted to obtain the best possible fit between the bone replica and the remaining proximal portion of the affected radius. This step allows detecting and correcting anatomical differences between the normal contralateral and affected limbs. This approach originates from the circumstance that the tumor often results in severe deformations of the affected radius; hence mirroring is then a designated solution for adequate implant design. A patient-specific limb sparing plate is created on the mirrored bone replica and the operated remaining radius to complete the endoprosthesis.

However, in some embodiments, for intracompartmental tumors that have not breached the bone cortex and in patients whose articular surfaces are intact, it is possible to design the implant by using the affected limb only. The approach to be taken is decided on a case-by-case basis.

To form 3D models of both affected and contralateral limbs, starting from a CT image, image segmentation is carried out, for example using Mimics (Materialise NV, Belgium), a highly accurate contour detection tool to separate bony from surrounding soft tissue structures. The outer surface of the limbs is typically automatically created, using for example the marching cube algorithm. The resulting tessellated limb models is exported into a computer assisted design tool for post processing. For example, the design tool used is CATIA v5 (Dassault Systems, France), a highly performant CAD/CAM software. With the help of the CAD tool, the tessellated limb models is smoothed and filled to create three dimensional solid body models. These will include the medullary cavity and its surrounding bony structures (diaphysis, metaphyses and epiphyses). Distinguishing these bone components, when performed, allows for a more durable prosthetic design.

The design of the implant is accomplished in two steps. First, a personalized cutting guide is designed. Second, the personalized implant is designed. The design of these components is, for example, carried out entirely in the CAD environment. Subsequently, both components are manufactured, for example using 3D printing or a CNC controlled machine, among other possibilities.

The cutting guide is highly advantageous in ensuring that the limb-sparing prosthesis will precisely fit the bone defect in terms of length and overall size. The cutting guide's shape is primarily influenced by the deformation created by the bone tumor and the cutting guide length depends on the resection margin established by the surgeon to prevent tumor recurrence. To create the cutting guide, the location at which osteotomy will occur is marked on the reconstructed affected limb geometry. Second, the profile of the cutting guide is drawn with the help of 2D sketches on the affected limb. The 3D solid model of the cutting guide is created using a multi-section solid extrusion feature. The 3D cutting guide extends beyond the osteotomy location and intersects with the limb. At the osteotomy site, a cutting slot pocket feature, wide enough for the bone saw blade to pass, is provided. During surgery, the cutting guide will be aligned using the distal tip of the ulna. Using this anatomical landmark is beneficial for alignment, because the tumor's pseudocapsule will remain intact. Lastly, a Boolean type logical subtraction between the affected limb and the cutting guide will be performed to create a seamless geometrical fit between the limb and the cutting guide. This fit helps in (i) centering the guide's cutting slot exactly at the osteotomy location and (ii) to lock the cutting guide in place while the veterinary surgeon performs the osteotomy.

The endoprosthesis (i) serves to span the bone defect caused by the surgical en bloc resection of the osteosarcoma, (ii) guarantees adequate biomechanical functionality of the spared limb, and (iii) minimizes the risk of implant failure and infection. Hence, the patient-specific prosthesis plays an important role in improving the patient's quality of life and function.

The endoprosthesis incorporates two main functional components, which are typically combined in one single part. Hence, no assembly of the implant is required, which greatly reduces the risk of failure, the creation of third body wear particles and surgical time. The first functional component is a mirror image of the normal contralateral radius. The second functional component is a personalized upgraded limb sparing plate. This patient-specific implant allows panarthrodesis (surgical joint stiffening) of the carpal joint.

The replica of the removed affected bone segment is created using a mirror image of the reconstructed normal contralateral solid limb model, obtained as described previously. At the proximal flat contact surface of the replica, a scaled extrusion of a portion of the medullary cavity is created (intramedullary stem) to enable a more solid connection between the implant and the intact bone. The limb sparing plate's locally variable profile and curvature is drawn on top of the reconstructed affected limb geometry using 2D sketches along the segment's longitudinal axis. During sketch creation, it is possible to implement variable degrees of extension in the antebrachial-carpal joint which will further improve limb function. The 3D model of the fixation plate is then generated, for example, with the help of a multi-section solid extrusion feature. Subsequently, the replica of the removed segment and the limb sparing plate are combined to form a single solid part with the help of a Boolean type logical addition. Lastly, mounting apertures, for example threaded countersunk hole features, are placed on the proximal and distal portions of the limb sparing plate for locking screw placement during surgery. To enable a solid connection between the implant and the remaining radius, at least one, for example two, screws from the radial side pass through threaded holes in the intramedullary pin, thereby acting similarly to an interlocking nail.

The cutting guide and endoprosthesis are manufactured using any suitable method. For example they are manufactured using two different additive manufacturing techniques. Prior to manufacturing, the solid 3D models of the cutting guide and endoprosthesis are surface tessellated and exported as separate .STL files. In some embodiments, the cutting guide is manufactured using fused deposition modeling (FDM), a cost-effective additive manufacturing technology capable of transforming biocompatible plastic materials.[21] In some embodiments, the endoprosthesis is manufactured using selective laser melting (SLM), a versatile manufacturing technology capable of direct manufacturing of parts made of biocompatible metals. An EOS280 SLM system can be utilized which uses a focused Nd-YAG laser to locally melt metal powder (e.g. stainless steel) evenly spread on a moveable building plate. To provide adequate implant stability while minimizing the implant weight and reduce the risk of excessive thermal stresses, a lattice structure can be implemented inside the replica of the removed bone. Upon completion of the manufacturing process, the endoprosthesis is cut off the building platform. Finally, all surfaces of the endoprosthesis may be finished using sand blasting followed by polishing. Such treatment results in a smooth and even surface that decreases the risk of bacterial adhesion and minimizes the risk of biofilm formation.

Designing patient-specific limb-sparing implants is advantageous over existing techniques, such as a combination "radius spacer-limb salvage plate" (RS-LSP), as it provides the closest to natural fit of the implant, a more physiological distribution of the mechanical load through the spared limb and hence a reduced risk of implant or bone failure. In addition to tailoring the plate curvature to that of the patient, the plate cross-section can also be minimized to create a low profile implant that is sufficiently strong to withstand applied loads. Moreover, using patient-specific limb-sparing implants avoids the use of the endoprostheses with fixed, predetermined length, which is a limitation of the implants on the market today. Consequently, the length of the bone resection is dictated by the length of the commercially-available implants instead of the optimal length of resection.

The present application cites many documents, the contents of which is hereby incorporated by reference in their entirety.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

FIG. 2, in a perspective environmental view, illustrates a cutting guide usable in the method of FIG. 1, the cutting guide being shown mounted to a radius and an ulna of a dog;

FIG. 3, in a top elevation view, illustrates the cutting guide of FIG. 2;

FIG. 4, in a bottom elevation view, illustrates the cutting guide of FIG. 2;

FIG. 5, in a perspective view, illustrates an endoprosthesis usable in the method of FIG. 1;

FIG. 6, in a perspective environmental view, illustrates the endoprosthesis of FIG. 5;

FIG. 7, in a perspective environmental view with a partial cutaway, illustrates the endoprosthesis of FIG. 5;

FIG. 8, in an alternative perspective environmental view, illustrates the endoprosthesis of FIG. 5;

FIG. 9, in an other alternative perspective environmental view, illustrates the endoprosthesis of FIG. 5.

DETAILED DESCRIPTION

Figure 1:
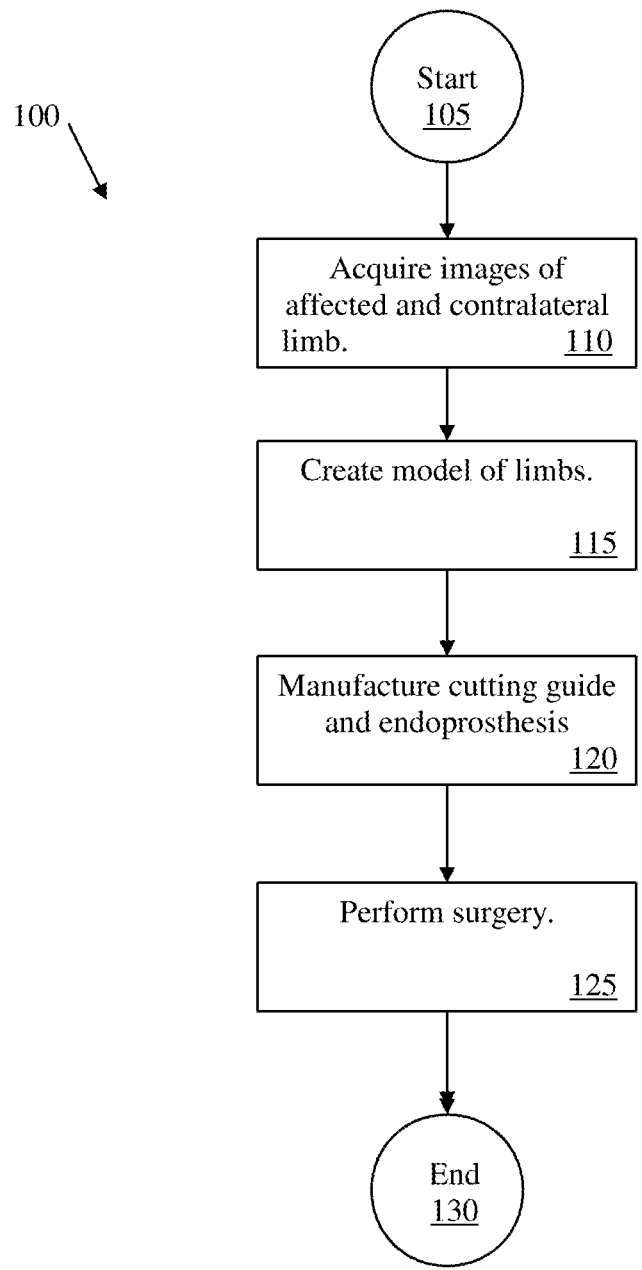
FIG. 1, in a flowchart, illustrates a limb sparing method in dogs in accordance with an embodiment of the present invention.

The present invention relates to limb sparing methods and devices. With reference to FIG. 1, the present invention implements a method 100 in which part of an affected limb is amputated and replaced by an endoprosthesis. The method starts at step 105. Then, at step 110, images of the affected limb and of the contralateral limb are acquired. The images are acquired using an imaging modality that allows creation of a 3D model of both limbs adjacent the portion of the affected limb to amputate, such as CT imaging, as performed in step 115. More specifically, in step 115, an affected limb 3D model is created, and a contralateral limb 3D model is created. These 3D models are used as basis for manufacturing respectively an endoprosthesis (in part from the mirror image of the contralateral limb 3D model and in part from the affected limb 3D model) and a cutting guide (from the affected limb 3D model), at step 120. Finally, at step 125, a surgical procedure is performed in which the cutting guide is positioned on the affected limb, directly on the bone, part of the affected bone is removed using surgical instruments, such as a surgical saw, and the prosthesis is secured to the remaining portion of the bone. Finally, the method ends at step 130.

While any suitable cutting guide may be manufactured, the cutting guide 200 shown in FIGS. 2 to 4 is well suited to guide removal of the distal portion 207 of the radius 202 (both shown in FIG. 2) in dogs and other similar animals. Such removal may be required for example because the distal portion 207 of the radius 202 is affected by a tumor.

Referring more specifically to FIG. 2, the distal part of the dog forelimbs includes two bones that are parallel to each other, the radius 202 and the ulna 204. As better seen in FIG. 6, for example, the ulna 204 is terminated by an ulnar distal tip known as the styloid process 206. The carpal bones 208 extend distally to the radius 202 and ulna 204, and the metacarpal bones 210 extend distally to the carpal bones 208. The forelimb bones are terminated distally by the phalanges 212.

Returning to FIG. 2, the cutting guide 200 includes a cut guiding portion 214, an opposed ulnar mounting portion 216 and a linking portion 218 therebetween, which are typically integrally formed together. Indeed, the radius 202 may be deformed by the tumor and as such its distal portion 207 is a poor choice for precise alignment of the cutting guide 200. Thus, a large portion of the cutting guide 200 is shaped for mounting to the ulna 204.

The cut guiding portion 214 is configured to abut against the radius adjacent the cut location where the radius 202 is to be cut during surgery. For example, the cut guiding portion 214 defines a slit 220 through which the blade of a saw (not shown in the drawings) can be inserted to cut through the radius 202. Thus, the slit 220 is configured, sized and positioned to be substantially adjacent the cut location when the cutting guide 200 is operatively mounted to the radius 202 and ulna 204. In some embodiments, the cut guiding portion 214 takes the form of a substantially plate-shaped element through which the slit 220 extends, but other configurations are within the scope of the invention. The slit 220 is typically generally perpendicular to the radius 202 when the cutting guide 200 is mounted to the radius 202 and ulna 204, but other orientations are within the scope of the invention.

The ulnar mounting portion 216 is substantially elongated and defines a substantially rectilinear main shaft 222 extending from the linking portion 218 and terminated, opposed to the cut guiding portion 214, by a hook 224. The hook 224 defines a hook recess 226 which opens generally towards the cut guiding portion 214. When the cutting guide is operatively mounted to the radius 202 and ulna 204, the main shaft 222 extends generally parallel to the ulna 204, and the ulnar distal tip (styloid process) 206 is received in the hook recess 226.

The linking portion 218 takes any suitable shape. For example, the linking portion 218 is substantially elongated and rectilinear and extends at an angle relative to the main shaft 222.

The cutting guide 200 is delimited by a cutting guide peripheral surface 228. The cutting guide peripheral surface 228 defines a bone facing portion 230, better seen in FIG. 4, which faces the radius 202 and ulna 204 when the cutting guide 200 is mounted thereto. The bone facing portion 230 has a shape, configuration and dimensions so that is conforms to the shape of the radius 202 and ulna 204. Thus, when the cutting guide 200 is mounted to the radius 202 and ulna 204, there is only one precise relative position between the cutting guide 200 and the radius 202 and ulna 204 that results in a precise fit therebetween. This ensures that the cutting guide 200 will not move easily relative to the radius 202 when the latter is cut, and ensures also that the slit 220 is precisely positioned at the right location prior to cutting the radius 202.

FIGS. 5 to 9 illustrates a prosthesis 300 in accordance with an embodiment of the present invention. The prosthesis 300 replaces a portion of the radius 202 that has been removed, for example using the cutting guide 200 of FIG. 2. With reference to FIG. 5 for example, the prosthesis 300 includes a fixation plate 302, a bone replica 304 extending from the fixation plate 302 and a fixation shaft 306 extending from the bone replica, in a generally parallel and spaced apart relationship relative to the fixation plate 302. In some embodiments, the prosthesis 300 is made of a single integrally extending piece of material, but a prosthesis made of many assembled components is also within the scope of the present invention.

The fixation plate 302 includes a plate proximal portion 308, a plate distal portion 310 and a plate intermediate portion 312 extending therebetween. The plate intermediate portion 312 supports the bone replica 304. The plate proximal and distal portions 308 and 310 are provided respectively proximally and distally relative to the plate intermediate portion 312 when the prosthesis 300 is operatively secured to the radius 202 and adjacent bones.

In a specific embodiment of the invention, the plate proximal portion 308 is substantially elongated and of substantially constant width, as better seen in FIG. 9. The plate proximal portion 308 is secured to the radius 202 in use. The plate intermediate portion 312 widens in a direction leading towards the plate distal portion 310. The plate distal portion 310 is substantially V-shaped and defines two arms 320, although plates having one or more than two arms 320 are within the scope of the invention. Each arm 320 is secured to a respective metacarpal bone 210 in use.

The bone replica 304 has a shape substantially similar to the shape the portion of the radius 202 that it replaces. This is achieved for example by having the bone replica 304 having the shape of a mirror image of the contralateral radius.

The fixation shaft 306 extends coaxially with the bone replica 304, at its proximal end, and is dimensioned to be inserted in the medulla 209 of the remaining portion of the radius 202, as seen in FIG. 7.

The plate proximal and distal portions 308 and 310 defines respectively opposed proximal inner and outer surfaces 322 and 324 and distal inner and outer surfaces 326 and 328, as seen in FIGS. 5 and 6. The proximal and distal inner surfaces 322 and 326 face respectively the radius 202 and the metacarpal bones 210 when the prosthesis 300 is fixed in the patient. To that effect, they are shaped to conform to the outer surface of these bones, using 3D models thereof constructed at step 115 of method 100. The plate proximal and distal portions 308 and 310 are mounted to the radius 202 and metacarpal bones 210 in any suitable manner. For example, mounting apertures 330 extend between the proximal inner and outer surfaces 322 and 324 and between the distal inner and outer surfaces 326 and 328. Although the prosthesis 300 includes 6 mounting apertures 330 in the plate proximal portion 308 and 6 mounting apertures 330 in each arm 320, any suitable number of mounting apertures 330 is usable. Fasteners, such as screws (seen in FIG. 10) are inserted through the mounting apertures 330 and in the radius 202 and metacarpal bones 210. In some embodiments, the fixation shaft 306 is provided with shaft apertures 332, seen in FIG. 5, each in register with one of the mounting apertures 330 so that the screws that are in register therewith can extend therethrough. Since fixation shaft 306 is usually shorter than the plate proximal portion 308, the number of shaft apertures 332 is typically smaller than the number of mounting apertures 330 in the plate proximal portion 308.

The fixation plate 302 can be chamfered at one or both ends to facilitate insertion between bones and soft tissues.

Example

Figure 10:
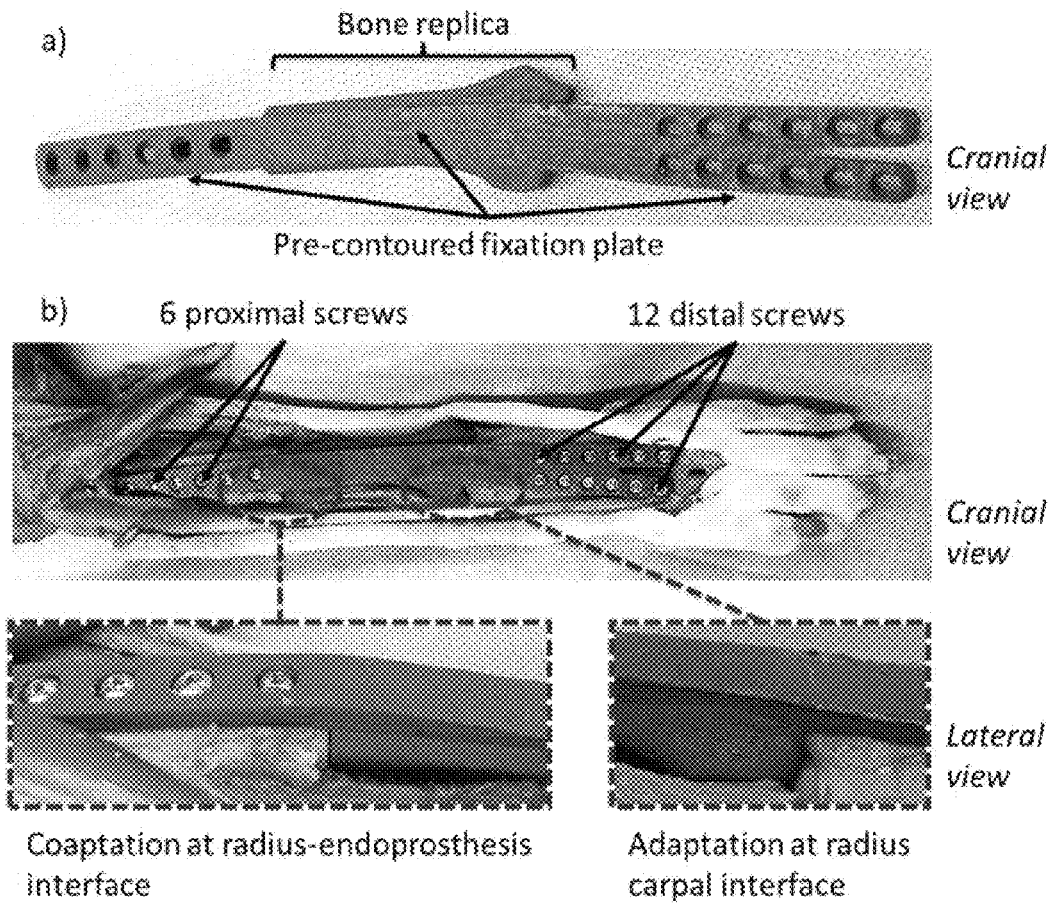
FIG. 10, in a series of photographs, illustrates some steps of the method of FIG. 1 performed on a cadaveric dog.

FIG. 10 includes photographs taken during performance of the method 100. Following a CT scan performed on a cadaveric thoracic limb from a dog euthanized for reasons unrelated to this study, a custom-made prosthesis 300 was created. Standard surgical technique utilized in dogs clinically afflicted with osteosarcoma of the distal radius was performed. Once a predetermined length of distal radius 202 was excised with the use of the cutting guide 200, the prosthesis 300 was positioned and fixated with 6 screws proximally (radius) and 12 screws distally (Metacarpals III and IV). Surgical technique took less than an hour and application/fixation of the prosthesis 300 was greatly facilitated by the use of a pre-contoured implant.

Although the present invention has been described hereinabove by way of preferred embodiments thereof, it can be modified, without departing from the spirit and nature of the subject invention as defined in the appended claims.

REFERENCES

1. Straw R C, Withrow S J: Limb-sparing surgery versus amputation for dogs with bone tumors. Vet Clin North Am Small Anim Pract 26:135-143, 1996.
2. Kuntz C A, Asselin T L, Dernell W S, et al: Limb salvage surgery for osteosarcoma of the proximal humerus: outcome in 17 dogs. Vet Surg 27:417-422, 1998.
3. Norton C, Drenen C M, Emms S G: Subtotal scapulectomy as the treatment for scapular tumour in the dog: a report of six cases. Aust Vet J 84:364-366, 2006.
4. Trout N J, Pavletic M M, Kraus K H: Partial scapulectomy for management of sarcomas in three dogs and two cats. J Am Vet Med Assoc 207:585-587, 1995.
5. Montinaro V, Boston S E, Buracco P, et al: Clinical outcome of 42 dogs with scapular tumors treated by scapulectomy: a Veterinary Society of Surgical Oncology (VSSO) retrospective study (1995-2010). Vet Surg 42:943-950, 2013.

6. Sivacolundhu R K, Runge J J, Donovan T A, et al: Ulnar osteosarcoma in dogs: 30 cases (1992-2008). J Am Vet Med Assoc 243:96-101, 2013.
7. Kirpensteijn J, Steinheimer D, Park R D, et al: Comparison of cemented and non-cemented allografts in dogs with osteosarcoma. Vet Comp Orthop Traumatol 11:178-184, 1998.
8. Lascelles B D, Dernell W S, Correa M T, et al: Improved survival associated with postoperative wound infection in dogs treated with limb-salvage surgery for osteosarcoma. Ann Surg Oncol 12:1073-1083, 2005.
9. Withrow S J, Liptak J M, Straw R C, et al: Biodegradable cisplatin polymer in limb-sparing surgery for canine osteosarcoma. Ann Surg Oncol 11:705-713, 2004.
10. Liptak J M D W, Ehrhart N, Withrow S J, Seguin B, Walsh P J, Kuntz C A: Canine appendicular osteosarcoma: curative-intent treatment. Compendium on Continuing Education 26:186-196, 2004.
11. Liptak J M, Dernell W S, Ehrhart N, et al: Cortical allograft and endoprosthesis for limb-sparing surgery in dogs with distal radial osteosarcoma: a prospective clinical comparison of two different limb-sparing techniques. Vet Surg 35:518-533, 2006.
12. Ehrhart N: Longitudinal bone transport for treatment of primary bone tumors in dogs: technique description and outcome in 9 dogs. Vet Surg 34:24-34, 2005.
13. Tommasini Degna M, Ehrhart N, Feretti A, et al: Bone Transport Osteogenesis for Limb Salvage Following Resection of Primary Bone Tumors: Experience with Six Cases (1991-1996). Vet Comp Orthop Traumatol 13:18-22, 2000.
14. Boston S E, Duerr F, Bacon N, et al: Intraoperative radiation for limb sparing of the distal aspect of the radius without transcarpal plating in five dogs. Vet Surg 36:314-323, 2007.
15. Buracco P, Morello E, Martano M, et al: Pasteurized tumoral autograft as a novel procedure for limb sparing in the dog: A clinical report. Vet Surg 31:525-532, 2002.
16. Hodge S C, Degner D, Walshaw R, et al: Vascularized ulnar bone grafts for limb-sparing surgery for the treatment of distal radial osteosarcoma. J Am Anim Hosp Assoc 47:98-111, 2011.
17. Seguin B, Walsh P J, Mason D R, et al: Use of an ipsilateral vascularized ulnar transposition autograft for limb-sparing surgery of the distal radius in dogs: an anatomic and clinical study. Vet Surg 32:69-79, 2003.
18. Seguin B, Walsh P J: Novel limb sparing technique for the distal radial site in dogs: lateral manus translation, Proceedings, European College of Veterinary Surgeons Annual Scientific Meeting, Nantes, France, 2009 (available from
19. Harrysson O A, Marcellin-Little D, Horn T: Applications of Metal Additive Manufacturing in Veterinary Orthopedic Surgery. JOM 67:647-654, 2015. 14
20. Liu X, Chu P K, Ding C: Surface modification of titanium, titanium alloys, and related materials for biomedical applications. Materials Science and Engineering: R: Reports 47:49-121, 2004.
21. M. Perez M B, D. Espalin, R. Winker, T. Hoppe, F. Medina, and R. Wicker: Sterilization of FDM-Manufactured Parts, in 23rd Int. Solid Freeform Fabr. Symp., Vol, 2012, pp 285-296.
22. Pooya H A, Séguin B, Mason D R, et al: Biomechanical Comparison of Cortical Radial Graft versus Ulnar Transposition Graft Limb-Sparing Techniques for the Distal Radial Site in Dogs. Veterinary Surgery 33:301-308, 2004.
23. Ehrhart N P, Ryan S D, Fan T M: Tumors of the skeletal system, in Withrow S J V D, Page R L (ed): Small Animal Clinical Oncology, Vol. St-Louis, Elsevier, 2013, pp 463-503.
24. Wilke V L, Robinson D A, Evans R B, et al: Estimate of the annual economic impact of treatment of cranial cruciate ligament injury in dogs in the United States. J Am Vet Med Assoc 227:1604-1607, 2005.
25. Rowell J L, McCarthy D O, Alvarez C E: Dog models of naturally occurring cancer. Trends Mol Med 17:380-388, 2011.

What is claimed is:
1. A cutting guide for guiding a cut in a radius, the radius being adjacent to an ulna, the cutting guide comprising:
a cut guiding portion, an opposed ulnar mounting portion and a linking portion extending therebetween;
the cutting guide being delimited by a cutting guide peripheral surface defining a bone facing portion, the bone facing portion being contoured to match the shape of the radius and ulna.
2. The cutting guide as defined in claim 1, wherein the cut guiding portion defines a slit extending therethrough.
3. The cutting guide as defined in claim 2, wherein the slit is substantially perpendicular to the radius when the cutting guide is operatively mounted thereto.
4. The cutting guide as defined in claim 1, wherein the linking portion is substantially elongated.

* * * * *